United States Patent [19]

Reifenberg

[11] 4,126,627

[45] Nov. 21, 1978

[54] PROCESS FOR PREPARING ALKALINE EARTH METAL MERCAPTIDES

[75] Inventor: Gerald H. Reifenberg, East Windsor, N.J.

[73] Assignee: Pennwalt Corporation, Philadelphia, Pa.

[21] Appl. No.: 875,271

[22] Filed: Feb. 6, 1978

[51] Int. Cl.$^2$ .................. C11C 3/00; C07C 149/06; C07C 149/28; C07C 149/30
[52] U.S. Cl. .............................. 260/399; 260/455 R; 260/583 EE; 260/609 D; 260/609 R; 560/103; 560/124; 560/265; 568/851
[58] Field of Search ........... 260/609 R, 609 D, 609 C, 260/399; 568/851; 560/265, 124, 103

[56] References Cited

U.S. PATENT DOCUMENTS

| | | | |
|---|---|---|---|
| 2,405,713 | 8/1946 | Russell | 568/851 |
| 3,136,740 | 9/1964 | Klemchuk | 260/609 D |

Primary Examiner—Lewis Gotts
Assistant Examiner—Molly C. Eakin
Attorney, Agent, or Firm—E. Leigh Hunt

[57] ABSTRACT

A process for preparing alkaline earth metal mercaptides in a two-step process, useful as synergists for organotin stabilizers in halogen containing resins such as polyvinyl chloride, comprising: (1) reacting a metallic oxide or hydroxide of the metal desired in the final mercaptide; a magnesium, aluminum or calcium alkoxide; and an alcohol to provide an alkoxide of the metal of the final mercaptide; and then (2) reacting the final alkoxide of (1) with a mercaptan to provide the desired metal mercaptide.

11 Claims, No Drawings

PROCESS FOR PREPARING ALKALINE EARTH METAL MERCAPTIDES

BACKGROUND OF THE INVENTION

As described in co-pending U.S. application Ser. No. 799,862 filed May 23, 1977 entitled "Heat Stabilizer Composition for Halogenated Resins", certain alkaline earth metal mercaptides are particularly useful as synergists in conjunction with certain sulfur containing organotin or antimony compounds.

In the above cited patent application, the alkaline earth metal mercaptides are perpared in accordance with the following reactions; wherein M is the alkaline earth metal:

$$M + 2R'OH \rightarrow M(OR')_2 + H_2 \quad (I)$$

$$M(OR')_2 + 2HSR \rightarrow M(SR)_2 + 2R'OH \quad (II)$$

The economics of carrying out such reactions commercially is less than ideal, as metals, M, are expensive. Other known methods by which certain metal alkoxides may be conveniently prepared are summarized by D. C. Bradley in "Progress in Inorganic Chemistry", Vol. 2 (edited by F. A. Cotton, Interscience Publishers, Inc., New York, N.Y., 1960, pp. 303ff). However, the only method cited by Bradley for preparing the alkaline earth metal alkoxides involves starting with the metal which is commercially uneconomical.

The oxides and hydroxides (hydrated or anhydrous) of the alkaline earth metals represent a much lower cost source for the metal M than the free metal itself.

The process of this invention provides a process for preparing the desired mercaptide starting with the corresponding metallic oxide or hydroxide; a relatively low-cost alkoxide of magnesium, aluminum or calcium; and an inexpensive alcohol. The other starting material required is a mercaptan of the corresponding desired metal mercaptide.

SUMMARY OF THE INVENTION

The process of this invention provides a simple two-step process for preparing the desired alkaline earth metal mercaptides useful as synergists for organotin stabilizers. The process provides excellent yields at substantial savings over other presently known methods. In the first step there is formed an alkoxide, $M(OR^1)_2$ by one of the following reactions:

$$MO + M^1(OR^1)_x + R^1OH \rightarrow M(OR^1)_2 + M^1(OH)_x \quad (III)$$

$$M(OH)_2 + M^1(OR^1)_x \xrightarrow{R^1OH} M(OR^1)_2 + M^1(OH)_x \quad (IV)$$

wherein:
$M^1$ is Mg, Al, or Ca;
M is Ca, Sr, or Ba;
$R^1$ is a hydrocarbon radical having from 1–20 carbon atoms and is selected from the group consisting of alkyl, cycloalkyl, or aralkyl, optionally substituted with inert noninterfering groups such as halogen and alkoxy; and, x is equal to the valence of $M^1$.

In the second step, the desired metal mercaptide is produced according to the reaction:

$$M(OR^1)_2 + 2HSR \rightarrow M(SR)_2 + 2HOR^1 \quad (V)$$

wherein:
R is a hydrocarbon radical having from 1 to 22 carbon atoms and is selcted from the group consisting of alkyl, cycloalkyl, aryl and mixed alkyl-aryl, said hydrocarbon radicals can optionally have a non-interfering substituent selected from the group consisting of halogen, $-XH$, $-XR^2$,

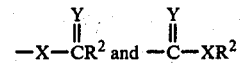

where $R^2$ is a hydrocarbon radical having from 1–20 carbon atoms and is selected from the group consisting of alkyl, alkenyl, cycloalkyl, aryl and mixed alkyl-aryl with the proviso that $R^2$ may be further substituted with inert substituents and X and Y are
independently selected from the group consisting of oxygen and sulfur.

The starting alkoxide $M^1(OR^1)_x$ may be readily prepared by a number of known methods. See Bradley, "Progress in Inorganic Chemistry", Vol. 2, referred to in the "Background of the Invention", supra.

The process of this invention is defined as a process for preparing alkaline earth metal mercaptides of the general formula $M(SR)_2$, wherein M is selected from the group consisting of barium, strontium, and calcium and R is a hydrocarbon radical having from 1 to 22 carbon atoms and is selected from the group consisting of alkyl, cycloalkyl, aryl and mixed alkyl-aryl, said hydrocarbon radicals can optionally have a non-interfering substituent selected from the group consisting of halogen, $-XH$, $-XR^2$,

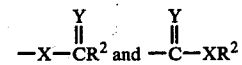

where $R^2$ is a hydrocarbon radical having from 1–20 carbon atoms and is selected from the group consisting of alkyl, alkenyl, cycloalkyl, aryl and mixed alkyl-aryl with the proviso that $R^2$ may be further substituted with inert substituents and X and Y are independently selected from the group consisting of oxygen and sulfur, comprising:

(1) forming a reaction mixture of:
   (a) a metal alkoxide of the general formula $M^1(OR^1)_x$, wherein $M^1$ is selected from the group consisting of magnesium, aluminum or calcium with the proviso that when $M^1$ is calcium M is barium or strontium: $R^1$ is a hydrocarbon radical having from 1–20 carbon atoms and selected from the group consisting of alkyl, cycloalkyl or aralkyl with the proviso that the hydrocarbon radical can be substituted with inert or noninterfering substituents; and x is a number equal to the valence of $M^1$; and
   (b) a metal oxide or hydroxide of the formula MO or $M(OH)_2$, wherein M is selected from the group consisting of barium, strontium or calcium; and
   (c) an alcohol of the general formula $R^1OH$ wherein $R^1$ is as above defined;

(2) subjecting the reaction mixture of (1) to reaction conditions that includes heating the mixture for sufficient time to provide $M^1(OH)_x$ and a metal alkoxide of the general formula $M(OR^1)_2$;

(3) forming a reaction mixture of: (a) the metal alkoxide $M(OR^1)_2$ of step (2), and (b) a mercaptan of the general formula RSH, wherein R is as above defined;

(4) subjecting the mixture of (3) to reaction conditions to provide the alkaline earth metal mercaptide of the general formula $M(SR)_2$; and then (5) separating the metal mercaptide $M(SR)_2$ from the mixture of step (4).

It is preferable for the alcohol, $R^1OH$ in reaction III above to be present in a molar excess to serve as a solvent for the reaction. In reaction IV above the alcohol serves solely as a solvent.

It is preferred that $R^1$ is selected from the above group to provide an alkoxide $M(OR^1)_x$ that is more soluble than the hydroxide $M^1(OH)_x$ in the mixture of step (2), to facilitate separation of the alkoxide $M(OR^1)_x$ from the mixture, in the event the alkoxide is isolated from the mixture prior to commencing step (3).

In step (2) above the reaction mixture is preferably heated to the boiling point of the alcohol, $R^1OH$ for a sufficient time to substantially complete the reaction.

It is preferred that M be barium or calcium whereas magnesium or aluminum are preferable for $M^1$. $R^1$ is preferably an alkyl group of 1 through 8 carbon atoms that can optionally be substituted with inert or non-interfering substituents.

After step (2) above it is preferred to separate the alkoxide $M(OR^1)_2$ from the mixture of step (2) prior to forming the reaction mixture of step (3).

DESCRIPTION OF THE PREFERRED EMBODIMENTS

In the preferred practice of this invention, the two reactants (according to reaction III or IV above) are added to the reactor in the ratio of x moles of MO or x/2 moles of $M(OH)_2$ per mole of $M^1(OR^1)_x$. In reaction III sufficient alcohol, $R^1OH$, is added to provide at least x moles (and preferably more, the excess acting as a solvent for the reaction as in reaction IV). The reaction mixture is heated to the boiling point of the alcohol for a period of time ranging from about 10 minutes to about 5 hours, typically 30 minutes to about 90 minutes, to ensure that the precipitation of $M^1(OH)_x$ is completed. The driving force for reaction III or IV is the precipitation of the hydroxide of $M^1$. The alkoxide $M(OR^1)_2$, should generally be soluble in the solvent in order to allow separation from $M^1(OH)_x$. $M^1(OR^1)_x$, MO and $M(OH)_2$ may or may not be soluble in $R^1OH$, the only requirement being that $M^1(OH)_x$ be less soluble so that reaction III or IV can be driven completely to the right (or nearly so). The hydroxide, $M^1(OH)_x$, is usually separated from the solution of the alkoxide $M(OR^1)_2$ by filtration, either hot or cold. Subsequently, the alkoxide $M(OR^1)_2$ may precipitate partially or entirely from solution. This is not critical and is of no importance to the success of this invention. In either case, it may be used in the reaction with RSH to produce the mercaptides.

In the preferred practice of reaction V, the mercaptan RSH may be added neat, or as a solution in $R^1OH$, or as a solution in an inert solvent such as pentane, hexane, heptane, cyclohexane, benzene, toluene, etc. (preferably one whose boiling range is approximately the same as $R^1OH$ or lower). The temperature of the reaction may range from about 0° to the boiling point of the solvent. The preferred temperature range is about 15° to about 60°C. The molar ratio of mercaptan RSH to metal alkoxide $M(OR^1)_2$ may range from >2:1 to 2:1 with the preferred ratio being 2:1.

At the end of the reaction, the reaction mixture is usually clear and colorless. If it is hazy, or if a slight precipitate is present, it may be clarified by filtration. The filtrate is then stripped under vacuum to afford the desired metal mercaptide.

It is also possible to run reactions III or IV and V sequentially without removing the hydroxide $M^1(OH)_x$ at the end of reaction III or IV. It is then removed at the end of reaction V, prior to removal of solvent. This one-pot procedure, however, does not usually yield as good a quality product.

In order to more clearly demonstrate the process of this invention, the following examples are presented. These are not to be construed as limiting the scope of this invention.

EXAMPLE 1

Into a one-liter, three-necked flask equipped with a mechanical stirrer, water condenser, and an addition funnel, are placed 1.22g (0.05 mole) of magnesium turnings, 100 ml of methanol, and a small crystal or iodine. The reaction mixture is heated cautiously, and in 5–10 minutes a vigorous evolution of hydrogen occurs to provide the alkoxide, $Mg(OCH_3)_2$. The source of heat is removed and in another 10 minutes all of the magnesium dissolves. The mixture is refluxed for 30 minutes to ensure complete reaction and then allowed to cool to room temperature.

In a separate vessel, under nitrogen, a solution of barium oxide in methanol is prepared by dissolving 15.33g (0.10 mole) of barium oxide in 150 ml of methanol. The dissolution, which is quite exothermic, is allowed to proceed for 10 minutes after which time the solution is filtered in order to remove a small amount of insolubles. The clear filtrate is placed in an addition funnel and is added over a period of 45 minutes to the magnesium methoxide solution formed in the first step.

The mixture is refluxed for 2.5 hours during which time magnesium hydroxide precipitates. After cooling to room temperature, the mixture is filtered.

The clear filtrate is placed in a 1-liter, three-necked flask equipped with a mechanical stirrer, water condenser, and an addition funnel. A solution of 40.87g (0.20 mole) of isooctyl thioglycolate in 100 ml of methanol is placed in the addition funnel and then added over a period of 45 minutes to the reaction solution. The resultant solution is concentrated under reduced pressure to give essentially a quantitative yield of barium bis(isooctyl thioglycolate).

Anal. Calcd. for $C_{20}H_{38}BaO_4S_2$: S(mercapto), 11.79. Found: S(mercapto), 10.31.

EXAMPLE 2

A solution of magnesium methoxide is prepared as described in Example 1 from 1.22g (0.05 mole) of magnesium turnings and 100 ml of methanol. To this solution is added over a period of 45 minutes a filtered solution of 15.33g (0.10 mole) of barium oxide in 150 ml of methanol, prepared as described in Example 1. The mixture is refluxed for 1.5 hours, cooled to room temperature, and filtered to remove magnesium hydroxide. The clear filtrate is transferred to a 1-liter, three-necked flask equipped with a mechanical stirrer, water condenser, and an addition funnel. A solution of 40.87g (0.20 mole) of isooctyl thioglycolate in 100 ml of methanol is added over a period of 45 minutes. After stirring for 1 hour, the slightly hazy solution is filtered and 54.0g of diethylene glycol dimethyl ether (diglyme) is added as diluent. Methanol is removed under reduced pressure to yield approximately a 1:1 barium bis(isooctyl thioglycolate)/diglyme mixture that weighs 96.4g. This mixture contains 48% barium bis(isooctyl thioglycolate) by titration with a standard iodine solution.

EXAMPLE 3

The procedure of this Example is identical to that described for Example 1 except that 2.02g (0.05 mole) of calcium metal turnings are used in place of magnesium turnings. There is obtained 51.3g of barium bis(isooctyl thioglycolate). Yield is about 94%.

EXAMPLE 4

A solution of magnesium methoxide in methanol is prepared as described in Example 1 from 1.22g (0.05 mole) of magnesium turnings and 150 ml of methanol. To this solution is added solid barium oxide (15.33g, 0.10 mole). The mixture is refluxed for 2.5 hours, cooled to room temperature, and filtered to remove magnesium hydroxide. The clear filtrate is placed in a 1-liter three-necked flask equipped with a mechanical stirrer, addition funnel, and water condenser. A solution of 40.87g (0.20 mole) of isooctyl thioglycolate in 150 ml of methanol is added over 45 minutes. After stirring for 1 hour longer, the slightly hazy solution is filtered and the filtrate concentrated under reduced pressure to provide an essentially quantitative yield of barium bis(isooctyl thioglycolate).

Anal. Calc. for $C_{20}H_{38}BaO_4S_2$: S(mercapto), 11.79. Found: S(mercapto), 10.23.

EXAMPLE 5

A solution of magnesium methoxide in methanol is prepared as described in Example 1 from 1.22g (0.05 mole) of magnesium turnings and 150 ml of methanol. Barium oxide (15.33g, 0.10 mole) is added followed by refluxing for 2.5 hours. After the mixture is cooled to room temperature, it is filtered to remove magnesium hydroxide. The filtrate is transferred to a 1-liter three-necked flask equipped with a mechanical stirrer, addition funnel, and a water condenser, and a solution of 38.46g (0.20 mole) of dodecyl mercaptan in a methanol-hexane mixture (100 ml: 30 ml) is added over a period of 45 minutes. After stirring for one hour, the solution is concentrated under reduced pressure to yield 49.4g (95% yield) of barium bis(dodecyl mercaptide)

Anal. Calcd. for $C_{24}H_{59}BaS_2$: S(mercapto), 12.33. Found: S(mercapto) 10.58.

EXAMPLE 6

Following the procedure in Example 4 except that aluminum (with a trace of $HgCl_2$ as catalyst) is used in place of magnesium, calcium in place of barium, and ethanol in place of methanol, there is obtained calcium bis(isooctyl thioglycolate).

EXAMPLE 7

Following the procedure outlined in Example 6 except that strontium is used in place of calcium, and methanol in place of ethanol, there is obtained strontium bis(isooctyl thioglycolate).

EXAMPLE 8

Following the procedure outlined in Example 4 except that dibutyl mercaptosuccinate is used in place of isooctyl thioglycolate, there is obtained barium bis(dibutyl mercaptosuccinate).

EXAMPLE 9

Following the procedure outlined in Example 7 except that dipropyl mercaptosuccinate is used in place of isooctyl thioglycolate, there is obtained strontium bis(dipropyl mercaptosuccinate).

EXAMPLE 10

Following the procedure outlined in Example 6 except that isooctyl 3-mercaptopropionate is used in place of isooctyl thioglycolate, there is obtained calcium bis(isooctyl 3-mercaptopropionate).

EXAMPLE 11

Following the procedure outlined in Example 4 except that aluminum (with a trace of $HgCl_2$ as catalyst) is used in place of magnesium, and isooctyl 3-mercaptopropionate in place of isooctyl thioglycolate, there is obtained barium bis(isooctyl 3-mercaptopropionate).

EXAMPLE 12

The procedure of Example 1 is repeated except that the below enumerated R groups in (RSH) are substituted for the one of Example 1:

methyl, ethyl, n-propyl, isopropyl, n-butyl, isobutyl, sec-butyl, tert-butyl, neopentyl, hexyl, octyl, decyl, dodecyl, tridecyl, hexadecyl, octadecyl, cyclopentyl, cyclohexyl, cyclooctyl, benzyl, β-phenylethyl, β-phenylpropyl, γ-phenylpropyl, 2-hydroxyethyl, 2-ethoxyethyl, carboethoxymethyl, carbooctoxymethyl, 1-carbooctoxyethyl, 2-carbooctoxyethyl, 2-dimethylaminoethyl, 2-stearoxyethyl, 2-acetoxyethyl, 2,3-diacetoxypropyl, 2,3-dilauroxypropyl, 2-hydroxy-3-octoxypropyl, 4-methylcyclohexyl, 4-methoxycyclohexyl, 2-methoxycyclopentyl, p-phenylbenzyl, o-methoxybenzyl, phenyl, tolyl, naphthyl, 1,2-dicarbobutoxyethyl, 1,1-dicarbobutoxymethyl, 1-carbobutoxy-2-carbooctoxyethyl, 1-carbomethoxyl-carbooctoxymethyl, 2-methylmercaptoethyl, 2-thiobooctoxyethyl, and thiocarbothiobutoxymethyl.

In each case the corresponding barium mercaptide is obtained.

EXAMPLE 13

The procedure of Example 1 is repeated except that the following $R^1$ groups are substituted for the methyl of Example 1: ethyl, n-propyl, isopropyl, n-butyl, isobutyl, sec-butyl, tert-butyl, neopentyl, hexyl, octyl, lauryl, oleyl, dodecyl, cyclopentyl, cyclohexyl, cycloheptyl, benzyl, β-phenylethyl, β-phenylpropyl, γ-phenylpropyl, 2-methoxyethyl, 2-chloroethyl, 2-phenoxyethyl, 2-methoxypropyl, 2-butoxypropyl, 2-dimethylaminoethyl, 3-diethylaminopropyl, 2(2'-ethoxyethoxy)ethyl, p-phenylbenzyl, p-methylbenzyl, o-ethylbenzyl.

In each case the desired mercaptide, barium bis(isooctyl thioglycolate), is obtained.

EXAMPLE 14

A solution of magnesium methoxide in methanol is prepared as described in Example 1 from 1.22g (0.05 mole) of magnesium turnings and 150 ml of methanol. To this solution is added solid barium hydroxide (8.57g, 0.05 mole). The mixture is refluxed for 2.5 hours, cooled to room temperature and filtered to remove magnesium hydroxide. The clear filtrate is placed in a 1-liter three-necked flask equipped with a mechanical stirrer, addition funnel, and water condenser. A solution of 20.43g (0.10 mole) of isooctyl thioglycolate in 150 ml of methanol is added over 45 minutes. After stirring for 1 hour longer, the slightly hazy solution is filtered and the filtrate concentrated under reduced pressure to provide an essentially quantitative yield of barium bis(isooctyl thioglycolate).

EXAMPLE 15

Following the procedure outlined in Example 14 except that calcium hydroxide (3.71g, 0.05 mole) is used in place of barium hydroxide, there is obtained calcium bis(isooctyl thioglycolate) in essentially quantitative yield.

I claim:

1. A process for preparing alkaline earth metal mercaptides of the general formula $M(SR)_2$, wherein M is selected from the group consisting of barium, strontium, and calcium and R is a hydrocarbon radical having from 1 to 22 carbon atoms and is selected from the group consisting of alkyl, cycloalkyl, aryl and mixed alkyl-aryl, said hydrocarbon radicals can optionally have a noninterfering substituent selected from the group consisting of halogen, —XH, —$XR^2$,

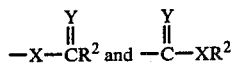

where $R^2$ is a hydrocarbon radical having from 1–20 carbon atoms and is selected from the group consisting of alkyl, alkenyl, cycloalkyl, aryl and mixed alkylaryl with the proviso that $R^2$ may be further substituted with inert substituents and X and Y are independently selected from the group consisting of oxygen and sulfur, comprising:

(1) forming a reaction mixture of:
(a) a metal alkoxide of the general formula $M^1(OR^1)_x$, wherein $M^1$ is selected from the group consisting of magnesium, aluminum or calcium with the proviso that when $M^1$ is calcium M is barium or strontium; $R^1$ is a hydrocarbon radical having from 1–20 carbon atoms and selected from the group consisting of alkyl, cycloalkyl, or aralkyl with the proviso that the hydrocarbon radical can be substituted with inert or noninterfering substituents: and x is a number equal to the valence of $M^1$: and
(b) a metal oxide or hydroxide of the formula MO, or $M(OH)_2$, wherein M is selected from the group consisting of barium, strontium or calcium; and
(c) an alcohol of the general formula $R^1OH$ wherein $R^1$ is as above defined:

(2) subjecting the reaction mixture of (1) to reaction conditions that include heating the mixture for sufficient time to provide $M^1(OH)_x$ and a metal alkoxide of the general formula $M(OR^1)_2$;

(3) forming a reaction mixture of: (a) the metal alkoxide $M(OR^1)_2$ of step (2), and (b) a mercaptan of the general formula RSH, wherein R is as above defined;

(4) subjecting the mixture of (3) to reaction conditions to provide the alkaline earth metal mercaptide of the general formula $M(SR)_2$; and then (5) separating the metal mercaptide $M(SR)_2$ from the mixture of step (4).

2. The process as defined in claim 1 wherein $R^1OH$ in step (1) (c) is present in molar excess to provide a solvent for the reaction.

3. The process as defined in claim 1 wherein $R^1$ is selected from the above group to provide an alkoxide $M(OR^1)_x$ that is more soluble than the hydroxide $M^1(OH)_x$ in the mixture of step (2), to facilitate separation of the alkoxide $M(OR^1)_x$ from the mixture, in the event that the alkoxide is isolated from the mixture prior to commencing the step (3).

4. The process as defined in claim 1 wherein in step (2) the reaction mixture is heated to the boiling point of the alcohol $R^1OH$ for sufficient time to substantially complete the reaction.

5. The process as defined in claim 1 wherein M is barium or calcium and $M^1$ is magnesium or aluminum.

6. The process as defined in claim 1 wherein M is barium or calcium, $M^1$ is magnesium or aluminum, and $R^1$ is an alkyl group of 1 through 8 carbon atoms that can optionally be substituted with inert or noninterfering substituents.

7. The process as defined in claim 1 wherein R is selected from the group consisting of:

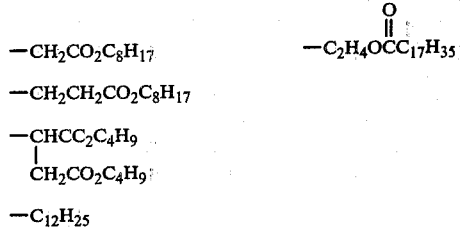

8. The process as defined in claim 7 wherein M is barium or calcium, $M^1$ is magnesium or aluminum, and $R^1$ is an alkyl group of 1 through 8 carbon atoms optionally substituted with inert or noninterfering substituents.

9. The process as defined in claim 7 wherein M is barium, $M^1$ is magnesium, $R^1$ is methyl or ethyl.

10. The process as defined in claim 8 wherein $R^1$ is selected from the above group to provide an alkoxide $M(OR^1)_2$ that is more soluble than the hydroxide $M^1(OH)_x$ in the mixture of step (2), to facilitate separation of the alkoxide $M(OR^1)_2$ from the mixture, in the event the alkoxide is isolated from the mixture prior to commencing step (3); and the alcohol $R^1OH$ in step (1) (c) of claim 1 is present in a molar excess to provide a solvent for the reaction.

11. The process as defined in claim 1, wherein after step 2, the alkoxide $M(OR^1)_2$ is separated from the mixture of step (2) prior to forming the reaction mixture of step (3).

* * * * *